United States Patent
Chen

(10) Patent No.: US 7,943,761 B2
(45) Date of Patent: May 17, 2011

(54) CELLULOSE BASED OPTICAL FILM MATERIAL AND METHOD FOR FORMING THE SAME

(75) Inventor: Chien-Tien Chen, Taipei (TW)

(73) Assignee: National Taiwan Normal University, Taipei (TW)

(*) Notice: Subject to any disclaimer, the term of this patent is extended or adjusted under 35 U.S.C. 154(b) by 802 days.

(21) Appl. No.: 11/550,796

(22) Filed: Oct. 19, 2006

(65) Prior Publication Data

US 2007/0117971 A1 May 24, 2007

Related U.S. Application Data

(60) Provisional application No. 60/737,766, filed on Nov. 18, 2005.

(51) Int. Cl.
*C08B 3/00* (2006.01)
*C08B 3/06* (2006.01)
*C08B 3/08* (2006.01)
*C08B 5/00* (2006.01)
*C08B 7/00* (2006.01)
*C07H 11/00* (2006.01)
*C07H 11/04* (2006.01)
*C07H 13/02* (2006.01)
*C07H 13/08* (2006.01)
*C07H 13/10* (2006.01)

(52) U.S. Cl. ............. 536/30; 536/34; 536/55.1; 536/62; 536/68; 536/69; 536/123.12

(58) Field of Classification Search .................. None
See application file for complete search history.

(56) References Cited

U.S. PATENT DOCUMENTS 5,458,887 A * 10/1995 Chen et al. .................. 424/464

OTHER PUBLICATIONS

Lee et al., "Pesticides combined with polymers. I. Synthesis of cellulose-6-(diethyl phosphorothioate)" Journal of the Faculty of Agriculture, Kyushu University (1974) vol. 19 No. 1, pp. 1-9.*

* cited by examiner

*Primary Examiner* — Eric S Olson
(74) *Attorney, Agent, or Firm* — WPAT, PC.; Justin King

(57) ABSTRACT

The present invention discloses a cellulose based optical film material with the following structure:

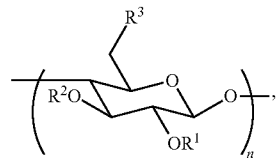

wherein $R^1$ is —H or —C(O)$R^4$, $R^4$ is alkyl or aryl; $R^2$ is —C(O)$R^5$, $R^5$ is alkyl or aryl; $R^3$ comprises one of the group consisting of: phosphinate based group, phosphonate based group, phosphonamide based group, phosphate based group, phosphoramide based group, carbamate based group, carbonate based group, and ester based group. Further, this invention also discloses a method for forming the cellulose based optical film material.

6 Claims, No Drawings

CELLULOSE BASED OPTICAL FILM MATERIAL AND METHOD FOR FORMING THE SAME

CROSS REFERENCE TO RELATED APPLICATIONS

This application claims the benefit of U.S. Provisional Application Ser. No. 60/737,766, filed on Nov. 18, 2005.

BACKGROUND OF THE INVENTION

1. Field of the Invention

The present invention is generally related to cellulose esters, and more particularly to cellulose based optical film materials.

2. Description of the Prior Art

Cellulose triacetate and derivatives exhibit less double refraction. Due to their moderate double refraction, cellulose triacetate derivatives have frequently been employed for production of protective optical films used for the polarizing plate of liquid crystal displays. Commonly, the polarizing plate has such a structure that a polarizing film comprised of a polyvinyl alcohol film and the like, in which iodine or dyes are absorbed and oriented, is laminated on both sides with transparent resin layers. Frequently employed as these transparent resin layers are protective films that are comprised of cellulose triacetate derivative films.

In recent years, development of liquid crystal displays to achieve a large-sized image screen of a high image quality has increasingly been made to produce advanced and compact monitors in lieu of the conventional nonportable CRT-based TVs. In conjunction with this, requirements for an advanced protective film for the polarizing plate in a liquid crystal display have become more stringent. Therefore, new cellulose based optical film materials of higher $T_g$ and more handy forming method are still in large demands in terms of both economic effect and utilization in display industry.

SUMMARY OF THE INVENTION

In accordance with the present invention, new cellulose based optical film materials and their forming method are provided to fulfill the requirements of this industry.

One objective of the present invention is to apply chemoselective ester-, phosphinate-, phosphonate-, phosphonamide-, phosphate-, phosphoramide-, carbonate-, and carbamate-forming method on partially hydrolyzed cellulose ester, so as to fabricate cellulose based optical film materials. The cellulose based optical film materials provided in this invention have good thermal property for its covalent bonding formed between functional groups and the cellulose main chain. Therefore, this present invention does have the economic advantages for industrial applications.

Accordingly, the present invention discloses a cellulose based optical film material with the following structure:

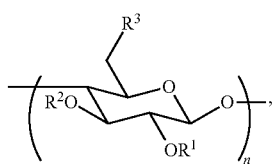

wherein $R^1$ is —H or —C(O)$R^4$, $R^4$ is alkyl or aryl; $R^2$ is —C(O)$R^5$, $R^5$ is alkyl or aryl; $R^3$ comprises one of the groups consisting of: phosphinate based group, phosphonate based group, phosphonamide based group, phosphate based group, phosphoramide based group, carbamate based group, carbonate based group, and ester based group. Further, this invention also discloses a method for forming the cellulose based optical film material.

DESCRIPTION OF THE PREFERRED EMBODIMENTS

What probed into the invention are cellulose based optical film materials and their forming method. Detailed descriptions of the production, structure and elements will be provided in the following in order to make the invention thoroughly understood. Obviously, the application of the invention is not confined to specific details familiar to those who are skillful in the art. On the other hand, the common elements and procedures that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In the first embodiment of the present invention, a cellulose ester with the following structure is disclosed:

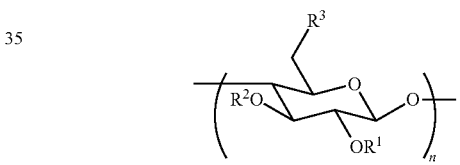

wherein $R^1$ is —H or —C(O)$R^4$, $R^4$ is alkyl or aryl; $R^2$ is —C(O)$R^5$, $R^5$ is alkyl or aryl; $R^3$ comprises one of the group consisting of: phosphinate based group, phosphonate based group, phosphonamide based group, phosphate based group, phosphoramide based group, carbamate based group, carbonate based group, and ester based group. $R^4$ and $R^5$ are the same or different, and the general formula of $R^4$ and $R^5$ is —(CH$_2$)$_n$CH$_3$, n is integer from 0 to 4. Furthermore, the mentioned cellulose ester has a value of weight average molecular weight-$M_w$/number average molecular weight-$M_n$ less than 3. Additionally, the cellulose ester can be used in optical film fabrication, and specifically used in protective film for polarizing plate.

In this embodiment, the general formula of the phosphinate based group is as following:

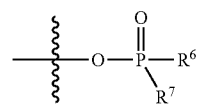

wherein $R^6$ and $R^7$ are the same or different, and $R^6$ and $R^7$ comprises one of the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or siloxane or thioether or carbamates.

In this embodiment, the general formula of the phosphonate/phosphonamide based group is as following:

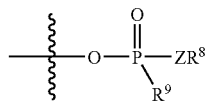

wherein Z is O or N, $R^8$ and $R^9$ are the same or different, and $R^8$ and $R^9$ comprises one of the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or siloxane or thioether or carbamates.

In this embodiment, the general formula of the phosphate/phosphoramide based group is as following:

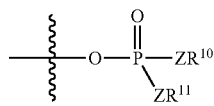

wherein Z is O or N, $R^{10}$ and $R^{11}$ are the same or different, and $R^{10}$ and $R^{11}$ comprises one of the group consisting of: linear alkyl, branched alkyl, cyclic alkyl, aryl moiety, hetero cycle, multiple fused ring, multiple fused ring with hetero atom(s), and alkyl with at least one substituent of alkene or alkyne.

In this embodiment, the general formula of the carbamate and carbonate based group is as following:

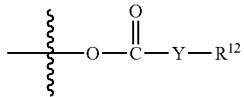

wherein Y is O or NH, and $R^{12}$ comprises one of the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or alkoxy or siloxane or ketone or thioether. Furthermore, some preferred carbonate based groups are listed as the following:

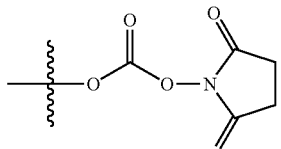 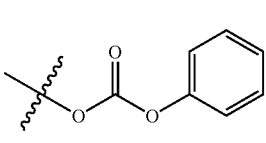

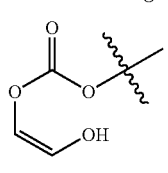 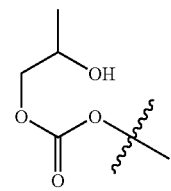

-continued

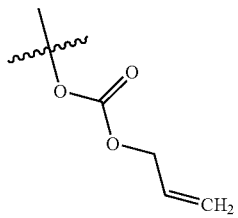

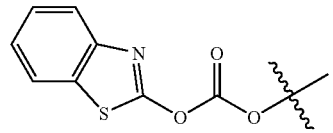

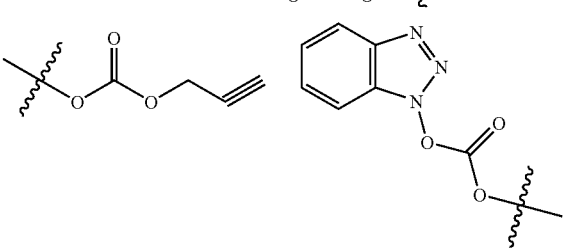

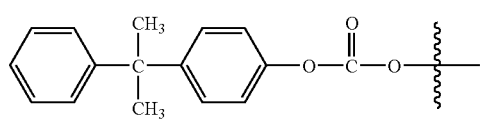

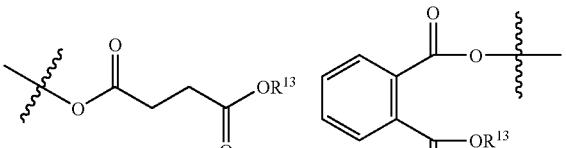

In this embodiment, the general formula of the ester based group comprises one of the following group:

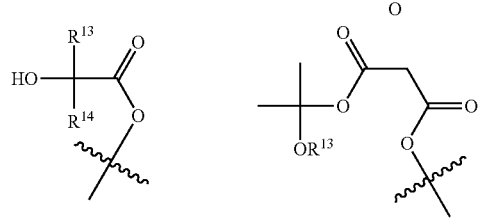

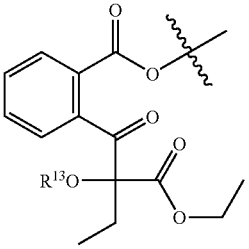 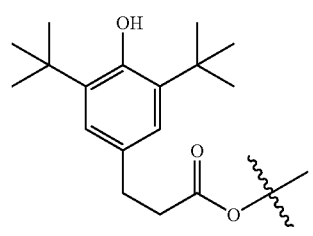

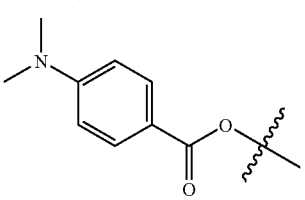 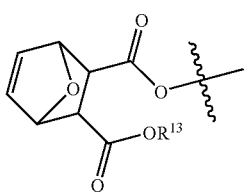

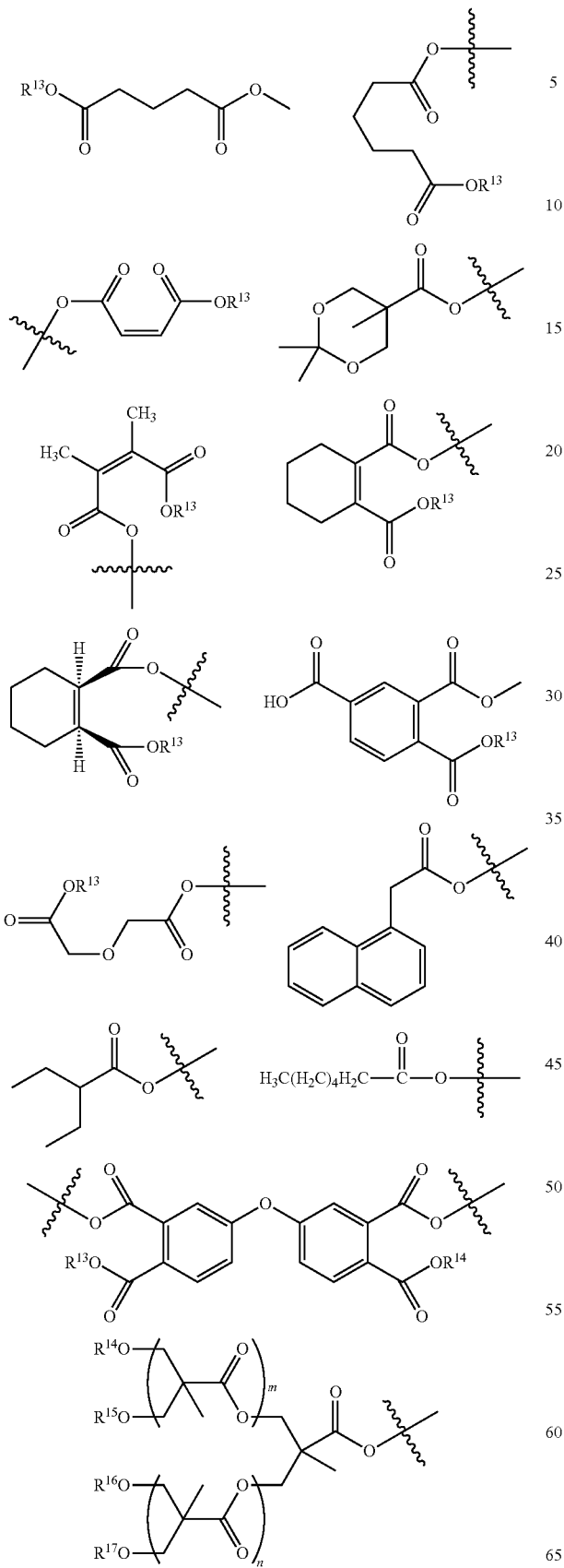
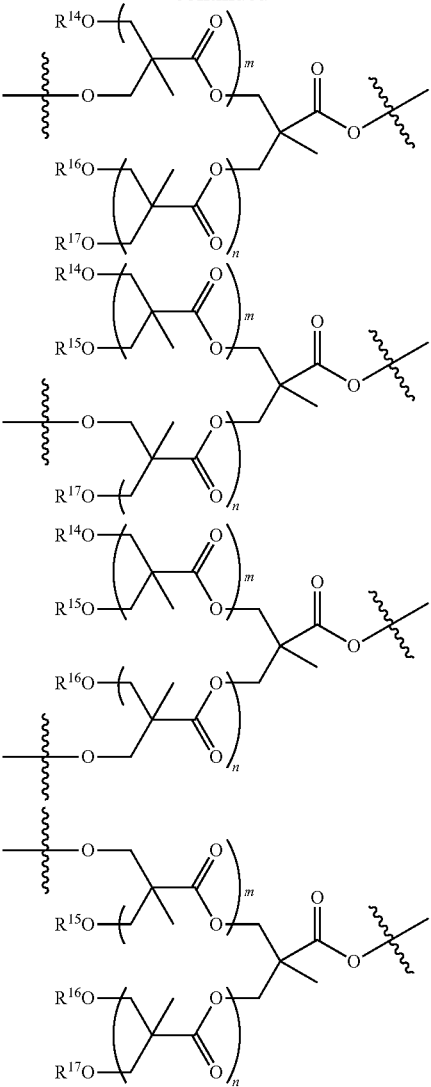

wherein $R^{13}$, $R^{14}$, $R^{15}$, $R^{16}$ and $R^{17}$ are the same or different, and $R^{13}$, $R^{14}$, $R^{15}$, $R^{16}$ and $R^{17}$ comprises one of the group consisting of: H, alkyl, and aryl.

In a second embodiment of the present invention, a method for forming a cellulose-based optical film material is disclosed. As shown in Scheme 1, an aliphatic anhydride is provided, and then the aliphatic anhydride is mixed with an aliphatic acid to form a mixture. The aliphatic anhydride comprises one of the groups consisting of: acetic anhydride, propionic anhydride, butyric anhydride, and valeric anhydride. The aliphatic acid comprises one of the groups consisting of: formic acid, acetic acid, propionic acid, and butyric acid. Next, a cellulose 1 is esterified with the mixture catalyzed by the first oxometallic complex $C^1$ to form an acylated cellulose 2, wherein R is alkyl or aryl. Afterwards, catalyzed by the second oxometallic complex $C^2$, the acylated cellulose 2 is partially hydrolyzed to form a partially hydrolyzed cellulose ester with at least one hydroxyl group per structure unit 3 or 5. Finally, one hydroxyl group per structure unit of the partially hydrolyzed cellulose ester is substituted, catalyzed by the third oxometallic complex $C^3$, with a reagent comprising one of the group consisting of: phosphinate/phosphinic halide-based compound, phosphonate/phosphonamide/halo-phosphonate/phosphonamidic halide-based compound, phosphate/phosphoramide/halo-phosphate/phosphorodiamidic halide-based compound, isocyanate based compound, anhydride based compound, ester based compound, carbonate based compound, and carboxylic acid based compound, so as to form the cellulose-based optical film material 4 or 6.

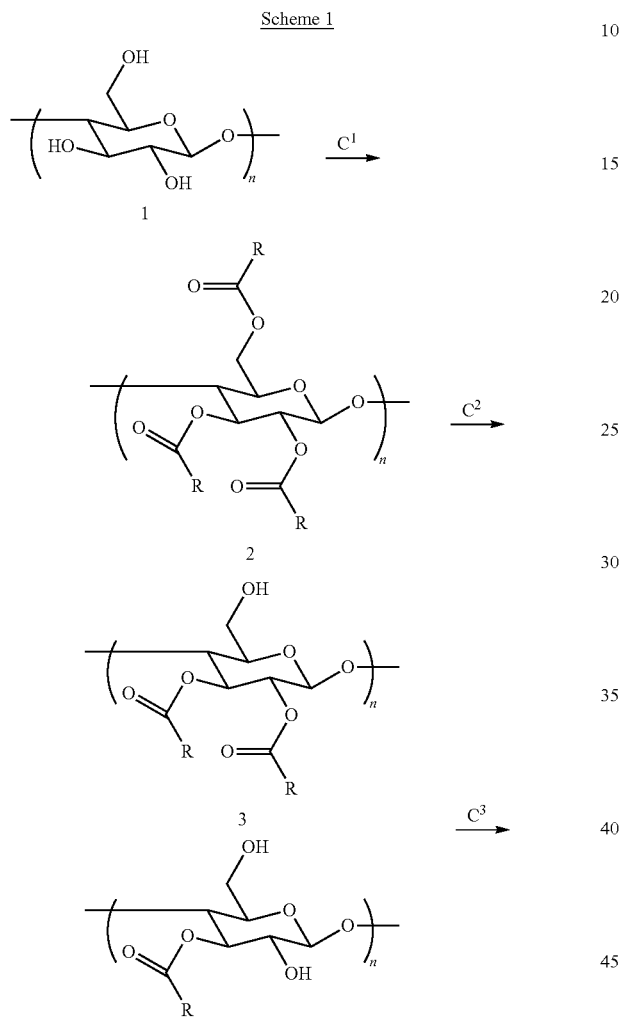

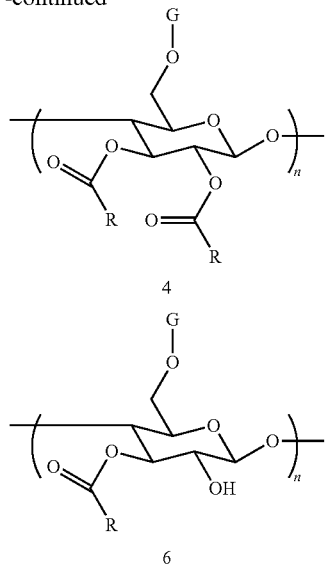

In this embodiment, the general formula of the first oxometallic complex, second oxometallic complex, and third oxometallic complex is $MO_mL^1{}_yL^2{}_z$, wherein M is selected from IVB, VB, VIB, VIIB or actinide series, m, y, z are integers, and m, y$\geq$1, z$\geq$0. $L^1$ comprises one of the group consisting of: OTf, X, $OC(O)R^{20}$, $R^{20}C(O)CHC(O)R^{21}$, OAc, OEt, O-iPr, butyl, $SO_3$—$R^{20}$, wherein X is halogen, and $R^{20}$ and $R^{21}$ are independently selected from the group consisting of: alkyl, and aryl. $L^2$ comprises one of the group consisting of: $H_2O$, $CH_3OH$, EtOH, THF, $CH_3CN$, $PPh_3$,

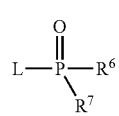

In this embodiment, when M is a transition element of group IVB, m=1, y=2, wherein preferred M comprises one of the groups consisting of: Ti, Zr, and Hf; when M is a transition element of group VB, there are two cases: in the case 1, m=1, y=2; and in the case 2, m=1, y=3. Preferred M comprises one of the group consisting of: V and Nb; when M is a transition element of group VI B, there are two cases: in the case 1, m=1, y=4; and in the case 2, m=2, y=2. Preferred M comprises one of the group consisting of: Mo, W, Cr; when M is a transition element of group VIIB, there are two cases: in the case 1, m=1, y=3; and in the case 2, m=2, y=1. Preferred M comprises one of the groups consisting of: Re and Mn. The preferred value of z is 2; when M is a transition element of actinide group, m=2, y=2, wherein preferred M comprises U.

In this embodiment, the general formula of the phosphinate/phosphinic halide-based compound is as following:

$$L-\overset{\overset{O}{\|}}{\underset{R^7}{P}}-R^6$$

wherein L is OR or halogen, R, $R^6$, and $R^7$ are independently selected from the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or siloxane or thioether or carbamates. Preferred structures are as following:

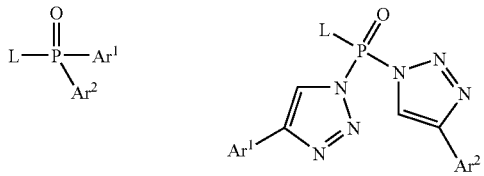

In this embodiment, the general formula of the phosphonate/phosphonamide/halo-phosphonate/phosphonamidic halide-based compound is as following:

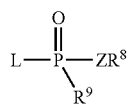

wherein Z is O or N, L is OR or halogen, R, $R^8$, and $R^9$ are the same or different, and R, $R^8$ and $R^9$ comprises one of the group consisting of: linear alkyl, branched alkyl, cyclic alkyl, aryl moiety, hetero cycle, multiple fused ring, multiple fused ring with hetero atom(s), and alkyl with at least one substituent of alkene or alkyne or siloxane or thioether or carbamates. Preferred structure is as following:

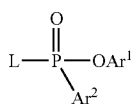

In this embodiment, the general formula of the phosphate/phosphoramide/halo-phosphate/phosphorodiamidic halide-based compound is as following:

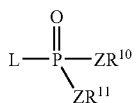

wherein Z is O or N, L is OR or halogen, R, $R^{10}$ and $R^{11}$ are the same or different, and R, $R^{10}$ and $R^{11}$ comprises one of the group consisting of: linear alkyl, branched alkyl, cyclic alkyl, aryl moiety, hetero cycle, multiple fused ring, multiple fused ring with hetero atom(s), and alkyl with at least one substituent of alkene or alkyne. Preferred structures are as following:

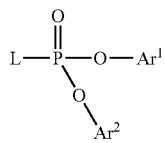

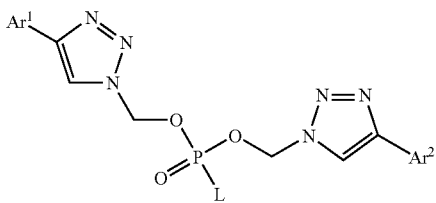

In this embodiment, the isocyanate based compound comprises one of the group consisting of:

(1) monoisocyanate based compound, comprising 3 configurations:

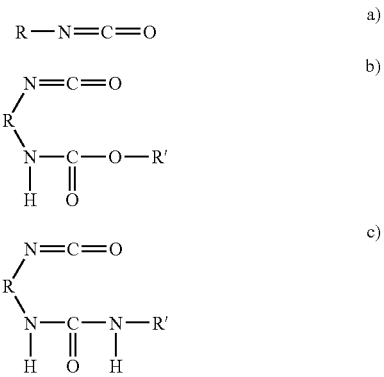

wherein R and R' are independently selected from the group consisting of: alkyl, aryl, hetero cycle, multiple fused ring, multiple fused ring with hetero atom(s).

(2) aromatic polyisocyanates: tolylene diisocyanate (TDI)(2,4- or 2,6-TDI), diphenylmethane diisocyanate (MDI)(4,4'- or 2,4'-MDI), polymeric MDI, xylylene diisocyanate (XDI), naphthylene diisocyanate (NDI)(usually 1,5-NDI), paraphenylene diisocyanate (PPDI), tetramethylxylylene diisocyanate (TMXDI), tolidine diisocyanate (TODI), 3,3'-dimethoxy-4,4'-biphenylene diisocyanate (3) alicyclic polyisocyanates: dicyclohexylmethane diisocyanate (HMDI)(4,4'- or 2,4'-HMDI), isophorone diisocyanate (IPDI), isopropylidene-bis-(4-cyclohexylisocyanate) (IPC), hydrogenated xylylene diisocyanate (hydrogenated XDI), cyclohexylene diisocyanate (CHPI)(usually 1,4-CHPI), 1,5-tetrahydonaphthalene diisocyanate (4) aliphatic polyisocyanates: hexamethylene diisocyanate (HDI), lysine diisocyanate (LDI), tetramethylene diisocyanate In this embodiment, the anhydride based compound comprises one of the group consisting of:

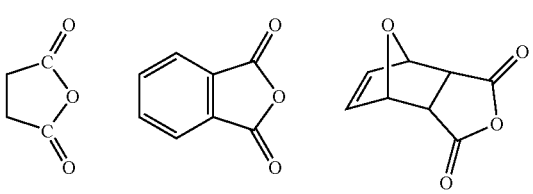

-continued

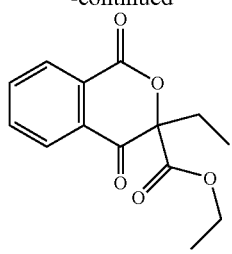

2) linear carbonate based compound, wherein the general formula of the linear carbonate based group is

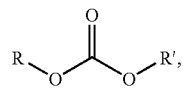

and R and R' are the same or different, and R and R' comprises one of the group consisting of:

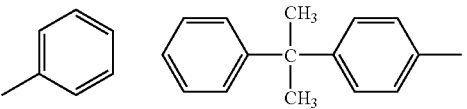

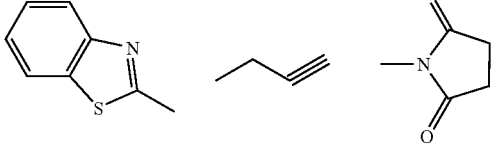

In this embodiment, the ester based compound comprises one of the group consisting of:

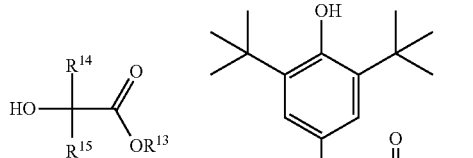

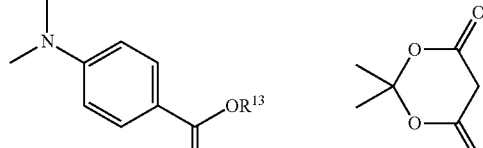

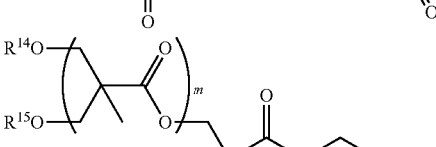

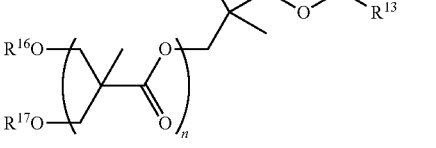

In this embodiment, the carbonate based compound comprises one of the group consisting of:
1) cyclic carbonate based compound:

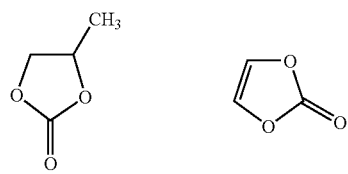

wherein $R^{13}$, $R^{14}$, $R^{15}$, $R^{16}$ and $R^{17}$ are the same or different, and $R^{13}$, $R^{14}$, $R^{15}$, $R^{16}$ and $R^{17}$ comprises one of the group consisting of: H, alkyl, and aryl. Additionally, when m=n=1, the structure formula of the last element of the mentioned group is as following:

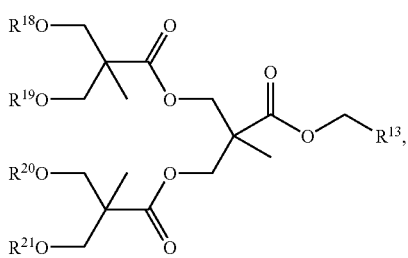

wherein $R^{13}$, $R^{18}$, $R^{19}$, $R^{20}$ and $R^{21}$ are the same or different, and $R^{13}$, $R^{18}$, $R^{19}$, $R^{20}$ and $R^{21}$ comprise one of the groups consisting of: H, alkyl, and aryl.

when m=n=2, the structure formula is as following:

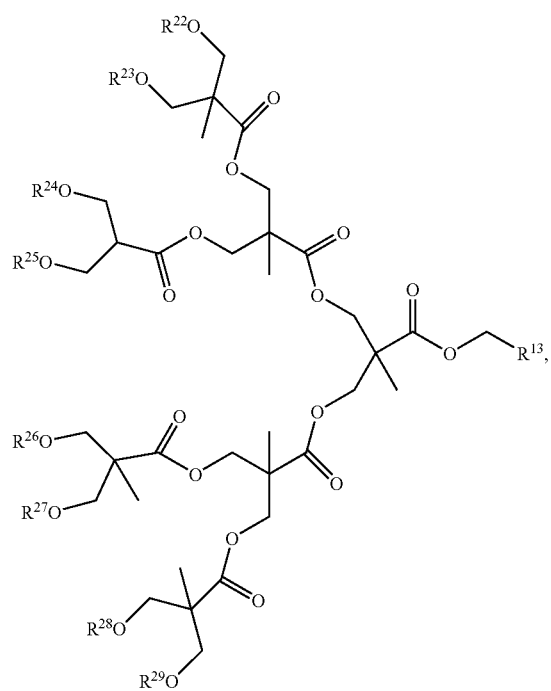

wherein $R^{13}$, $R^{22}$, $R^{23}$, $R^{24}$, $R^{25}$, $R^{26}$, $R^{27}$, $R^{28}$ and $R^{29}$ are the same or different, and $R^{13}$, $R^{22}$, $R^{23}$, $R^{24}$, $R^{25}$, $R^{26}$, $R^{27}$, $R^{28}$ and $R^{29}$ comprise one of the groups consisting of: H, alkyl, and aryl.

when m=n=3, the structure formula is as following:

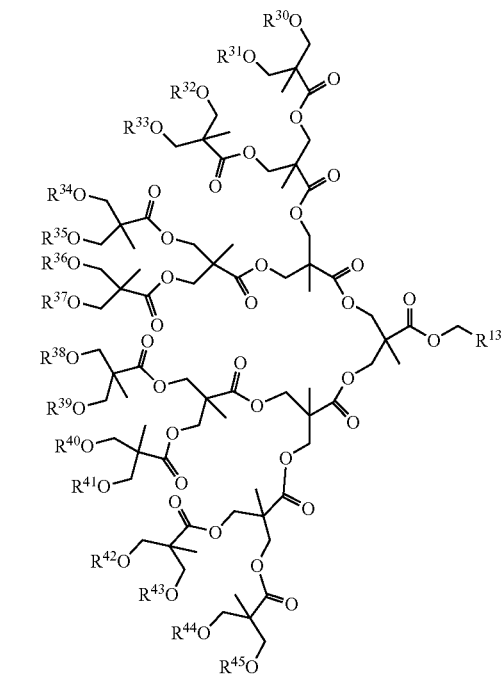

wherein $R^{13}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ are the same or different, and $R^{13}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$ and $R^{45}$ comprise one of the groups consisting of: H, alkyl, and aryl.

In this embodiment, the carboxylic acid based compound comprises one of the groups consisting of:

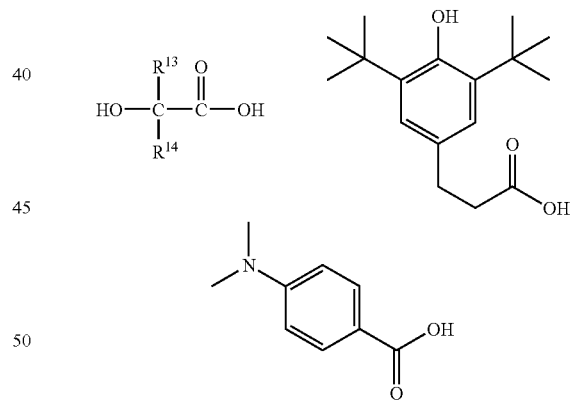

wherein $R^{13}$ and $R^{14}$ the same or different, and $R^{13}$ and $R^{14}$ comprise one of the groups consisting of: H, alkyl, and aryl.

EXAMPLE

Cellulose Acetate

In two-neck 100 mL round bottom flask, 3 g of cellulose was dissolved in 20 mL mixture of acetic acid and acetic anhydride (1:1) in to this 1 mol % of first oxometallic complex (30 mg) was added. Mixture was heated at 100~120° C. for 24 hours. After completion, reaction was quenched by pouring it in ice cold solution of saturated $NaHCO_3$ (100 mL×3) for 30 min, filter the solid product and wash with cold water for 5~6 times. White solid product was collected and dried under vacuum to give cellulose acetate with 6 g (90-92%).

Partial Hydrolysis

To a solution of cellulose acetate (1 g) in 20 mL $CH_2Cl_2$ in a two-necked, round-bottomed flask was added 10 mL of alcohol (C1-C5) and 5~10 mol % second oxometallic complex (20 mg) was added. Reaction was monitored by $^1H$ NMR up to 36 hours (beyond 36 h over hydrolysis was observed) at 40-130° C., after completion solvent was removed under vacuum (the resultant crude product can be used directly for next step). The transparent solid product was washed with $CH_2Cl_2$ till colorless.

Substitution

Hydrolyzed cellulose acetate was taken in two-necked flask and dissolved in acetonitrile. 5 to 10 mol % third oxometallic complex (20 mg) was added to the reaction mixture and the mixture was allowed to be stirred at room temperature for 2 days. After completion, solvent was removed by vacuum and the crude solid was extracted with chloroalkanes or ketones (C3-C5) (depending on solubility of the product) to give the desired colorless transparent product (phosphorylated and carbamylated).

In a third embodiment of the present invention, a cellulose-based formula for optical film fabrication is disclosed. The formula comprises a first cellulose ester, a second cellulose ester, and a partially hydrolyzed cellulose ester. The first cellulose ester has the following structure:

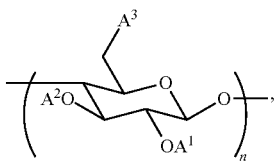

wherein $A^1$ is —H or —C(O)$A^4$, $A^4$ is alkyl or aryl; $A^2$ is —C(O)$A^5$, $A^5$ is alkyl or aryl; $A^3$ is carbonate based group or ester based group. The second cellulose ester has the following structure:

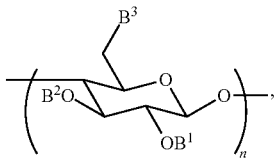

wherein $B^1$ is —H or —C(O)$B^4$, $B^4$ is alkyl or aryl; $B^2$ is —C(O)$B^5$, $B^5$ is alkyl or aryl; $B^3$ comprises one of the group consisting of: phosphinate based group, phosphonate based group, phosphonamide based group, phosphate based group, phosphoramide based group, carbamate based group. The partially hydrolyzed cellulose ester has at least one hydroxyl group per structure unit. Additionally, the formula can further comprise any one or any combination of the group consisting of: chloroalkanes, DMF, and alcohol (C1-C5). Moreover, the formula can further comprise mannose and/or xylose.

In the above preferred embodiments, the present invention applies chemoselective ester-, phosphinate-, phosphonate-, phosphonamide-, phosphate-, phosphoramide-, carbonate-, and carbamate-forming method on partially hydrolyzed cellulose ester, so as to fabricate cellulose based optical film materials. The cellulose based optical film materials provided in this invention have good thermal property for its covalent bonding formed between functional groups and the cellulose main chain. Therefore, this present invention does have the economic advantages for industrial applications.

To sum up, the present invention discloses a cellulose based optical film material with the following structure:

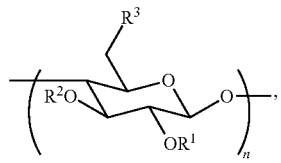

wherein $R^1$ is —H or —C(O)$R^4$, $R^4$ is alkyl or aryl; $R^2$ is —C(O)$R^5$, $R^5$ is alkyl or aryl; $R^3$ comprises one of the group consisting of: phosphinate based group, phosphonate based group, phosphonamide based group, phosphate based group, phosphoramide based group, carbamate based group, carbonate based group, and ester based group. Further, this invention also discloses a method for forming the cellulose based optical film material.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A cellulose-based composition for optical film fabrication, comprising:
   a first cellulose ester with the following structure:

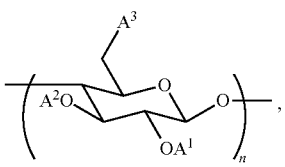

wherein n =500-800 with glucose as the monosaccharide unit,
$A^1$ is —H or —C(O)$A^4$, $A^4$ is alkyl or aryl,
$A^2$ is —C(O)$A^5$, $A^5$ is alkyl or aryl,
$A^3$ is carbonate group or ester group;
a second cellulose ester with the following structure:

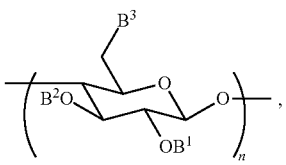

wherein n =500-800 with glucose as the monosaccharide unit,
$B^1$ is —H or —C(O)$B^4$, $B^4$ is alkyl or aryl,
$B^2$ is —C(O)$B^5$, $B^5$ is alkyl or aryl, $B^3$ comprises one of the groups consisting of: phosphinate group, phosphonate group, phosphonamide group, phosphate group, phosphoramide group, carbamate group; and a partially hydrolyzed cellulose ester with at least one hydroxyl group per monosaccharide unit.

2. The composition as claimed in claim 1, further comprising chloroalkanes as solvent.

3. The composition as claimed in claim 1, further comprising alcohol ($C_1$-$C_5$) as solvent.

4. The composition as claimed in claim 1, wherein the first cellulose ester and the second cellulose ester further comprise mannose monosaccharides.

5. The composition as claimed in claim 1, further comprising N,N-dimethylformamide (DMF) as solvent.

6. The composition as claimed in claim 1, wherein the first cellulose ester and the second cellulose ester further comprise xylose monosaccharides.

* * * * *